United States Patent [19]

Ozawa et al.

[11] Patent Number: 4,464,386

[45] Date of Patent: Aug. 7, 1984

[54] INSECTICIDAL 3-DIFLUOROMETHOXYPHENYL-1-PHENYLCARBAMOYL-2-PYRAZOLINES

[75] Inventors: Kiyomi Ozawa; Yasuyuki Nakajima; Makoto Tsugeno; Shigeru Ishii; Masataka Hatanaka, all of Funabashi, Japan

[73] Assignee: Nissan Chemical Industries, Ltd., Tokyo, Japan

[21] Appl. No.: 455,735

[22] Filed: Jan. 5, 1983

Related U.S. Application Data

[63] Continuation-in-part of Ser. No. 292,710, Aug. 13, 1981, Pat. No. 4,407,813.

[51] Int. Cl.$^3$ .................. C07D 231/06; A01N 43/56
[52] U.S. Cl. .................................. 424/273 P; 548/379
[58] Field of Search ...................... 424/273 P; 548/379

[56] References Cited

U.S. PATENT DOCUMENTS 4,140,792  2/1979  Sirrenberg et al. .............. 424/273 P

FOREIGN PATENT DOCUMENTS 1108154   9/1981  Canada ........................... 424/273 P
WO79/00858 11/1979 PCT Int'l Appl. ............. 424/273 P

*Primary Examiner*—John M. Ford
*Assistant Examiner*—Kurt G. Briscoe
*Attorney, Agent, or Firm*—Oblon, Fisher, Spivak, McClelland & Maier

[57] ABSTRACT

Pyrazoline derivatives useful as insecticides having the formula

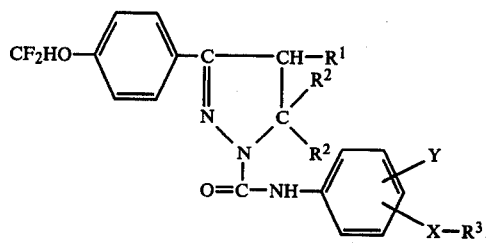

[I]

wherein $R^1$ represents hydrogen atom, a lower alkyl group, $(CH_2)_nCN$ group, $(CH_2)_nOR$ group, phenyl group or a halogen-substituted phenyl group; $R^2$ represents hydrogen atom or methyl group; Y represents hydrogen atom or chlorine atom; X represents oxygen atom, sulfur atom, sulfinyl or sulfonyl group; $R^3$ represents a halogen-substituted lower alkyl group; and n is integer 1 to 3 and R represents a lower alkyl group.

14 Claims, No Drawings

INSECTICIDAL 3-DIFLUOROMETHOXYPHENYL-1-PHENYL-CARBAMOYL-2-PYRAZOLINES

This application is a continuation-in-part of application Ser. No. 292,710, filed Aug. 13, 1981, now U.S. Pat. No. 4,407,813.

The present invention relates to pyrazoline derivatives a production thereof and an insecticide containing a pyrazoline derivative thereof as an active ingredient.

Various chemicals for insecticides have been studied and developed for a long time. These insecticides have been contributed for improvement of a productivity of agricultural crops. However, a development of a chemical having superior insecticidal activity has been required.

It has been known that 1-carbamoyl-2-pyrazoline derivatives are effective as insecticides in Japanese Unexamined Patent Publication No. 87028/1973, No. 41358/1976 and No. 87166/1977, etc. as pyrazoline derivatives.

It is an object of the present invention to provide insectidal compounds which have excellent effects and low toxicity to mammals and fishes.

The foregoing object of the present invention has been attained by providing pyrazoline derivatives having the formula [I],

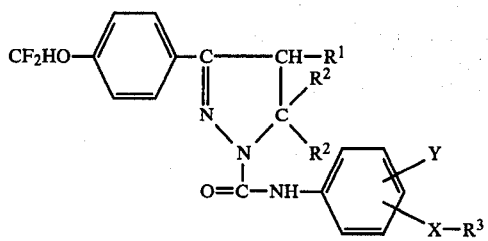

[I]

wherein $R^1$ represents hydrogen atom, a lower alkyl group, $(CH_2)_nCN$ group, $(CH_2)_nOR$ group, phenyl group or a halogen-substituted phenyl group; $R^2$ represents hydrogen atom or methyl group; Y represents hydrogen atom or chlorine atom; X represents oxygen atom, sulfur atom, sulfinyl or sulfonyl group; $R^3$ represents a halogen-substituted lower alkyl group; and n is integer 1 to 3 and R represents a lower alkyl group.

The compounds of the present invention have been produced by the following reaction scheme (1) or (2).

Scheme (1)

(The case of the formula [I] wherein X represents oxygen atom or sulfur atom.)

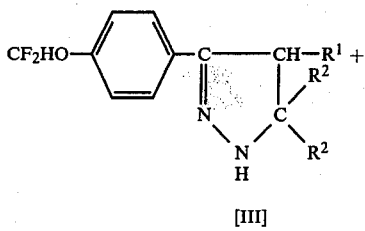

[III]

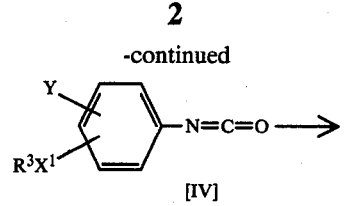

[IV]

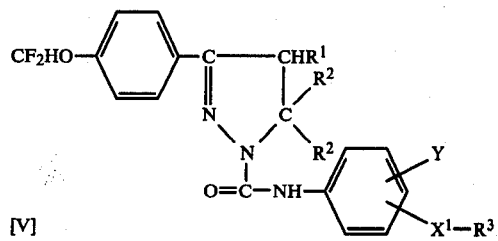

[V]

wherein $R^1$, $R^2$, $R^3$ and Y are defined above; $X^1$ represents oxygen atom or sulfur atom.

Scheme (2)

(The case of the formula [1] wherein X represents sulfinyl group or sulfonyl group.)

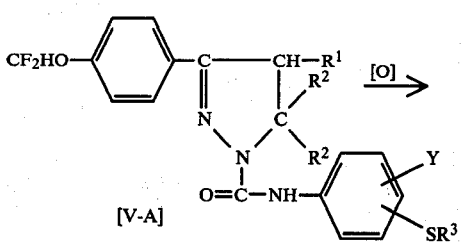

[V-A]

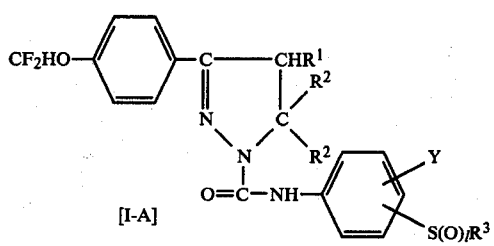

[I-A]

wherein l is integer 1 to 2; $R^1$, $R^2$, $R^3$ and Y are defined above.

The pyrazoline derivatives having the formula [V] can be produced by reacting 2-pyrazoline derivative having the formula [III] with phenylisocyanate having the formula [IV] in the presence or absence of an inert solvent.

Suitable insert solvents include ethyl ether, benzene, toluene, acetonitrile, pyridine, dichloromethane, chloroform and carbon tetrachloride.

The reaction temperature and the reaction time can be selected depending upon the starting material. Usually, the reaction temperature is in a range of −20° C. to 100° C. The reaction time is preferably in a range of 0.5 to 24 hours.

The compounds having the formula [I] wherein X is —SO— or —$SO_2$—, can be obtained by oxidizing the compound having the formula [V-A] obtained by the scheme (1) with an oxidizing agent such as hydrogen peroxide-acetic acid or meta chloroperbenzoic acid.

The 2-pyrazoline derivatives having the formula [III] as the starting material used in the reaction scheme (1)

are also insecticidal compounds which can be produced, for example, by the following reaction schemes.

Scheme (3)

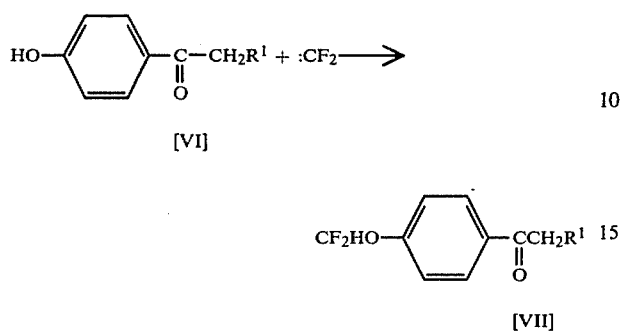

wherein $R^1$ represents hydrogen atom, a lower alkyl group, phenyl group, halogen-substituted phenyl group, a cyano alkyl group or lower alkoxy alkyl group.

Scheme (4-A)

The compound having the formula [III] wherein $R^1$ represents phenyl group or halogen-substituted phenyl group and $R^2$ represents hydrogen atom;

[VII-A]

[III-A]

wherein $R^1_A$ represents phenyl group or a halogen-substituted phenyl group.

Scheme (4-B)

The compounds having the formula [III] wherein $R^1$ represents phenyl or a halogen-substituted phenyl group; $R^2$ represents methyl group.

[VII-A]

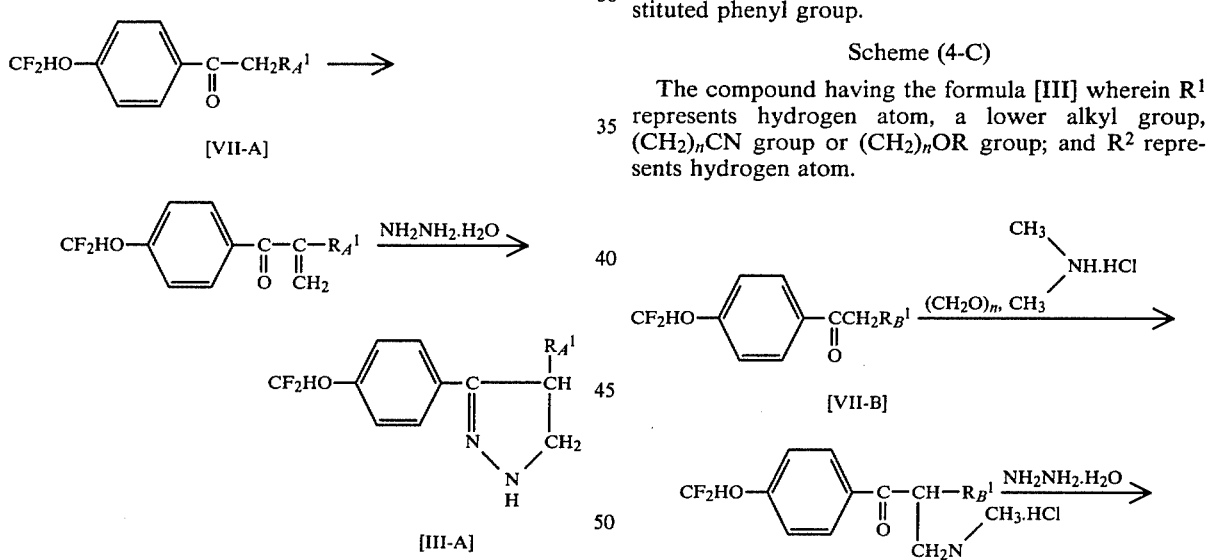

[III-B]

wherein $R^1_A$ represents phenyl group or a halogen-substituted phenyl group.

Scheme (4-C)

The compound having the formula [III] wherein $R^1$ represents hydrogen atom, a lower alkyl group, $(CH_2)_nCN$ group or $(CH_2)_nOR$ group; and $R^2$ represents hydrogen atom.

[VII-B]

[III-C]

wherein $R^1_B$ represents hydrogen atom, a lower alkyl group, $(CH_2)_nCN$ group or $(CH_2)_nOR$ group.

The 4-difluoromethoxy acyl benzene having the formula [VII] can be produced according to the scheme (3).

The 2-pyrazoline derivatives having the formula [III] can be produced by selecting from the schemes (4-A), (4-B) and (4-C) depending upon the substituent groups of $R^1$ and $R^2$ in the formula [III].

In the scheme (4-A), the 2-pyrazoline derivative having the formula [III-A] is produced by reacting formaldehyde in an acidic medium in the presence of a solvent and a catalyst and reacting the product with hydrazine in a solvent such as an alcohol such as ethanol and propanol.

In the scheme (4-B) the acrylophenone derivative is produced by reacting isopropyl iodide in the presence of a base such as NaH followed by the reaction of bromine and then, reacting a dehydrogen bromide agent such as LiCl. The 2-pyrazoline derivative having the formula [III-B] is produced by reacting the resulting product with hydrazine at room temperature in the presence of a base such as 50% NaOH solution with a solvent such as methanol etc.

In the scheme (2-C), the dimethyl aminomethylated product is produced by reacting dimethylamine hydrochloride with paraformaldehyde in a solvent such as ethanol in the presence of an acid catalyst such as conc. hydrochloric acid and then, hydrazine is added to the product in a solvent such as methanol in the presence of a base such as 50% NaOH aqueous solution and the mixture is heated to obtain 2-pyrazoline derivative having the formula [III-C].

The 2-pyrazoline derivatives having the formula [III] produced by these reactions can be isolated and purified. In many cases, however, these products are unstable at room temperature. Thus, certain products should be stored under nitrogen atmosphere at a low temperature. In a practical operation, the pyrazoline derivative having the formula [I] of the present invention can be produced without an isolation and purification of the 2-pyrazoline derivative [III] by reacting the product with a phenyl isocyanate derivative.

The compounds having $OCF_2Br$ or $SCF_2Br$ group as $X_1$-$R^3$ in the phenylisocyanate derivative having the formula [IV] are insecticidal compounds. The compounds can be produced by the following Scheme.

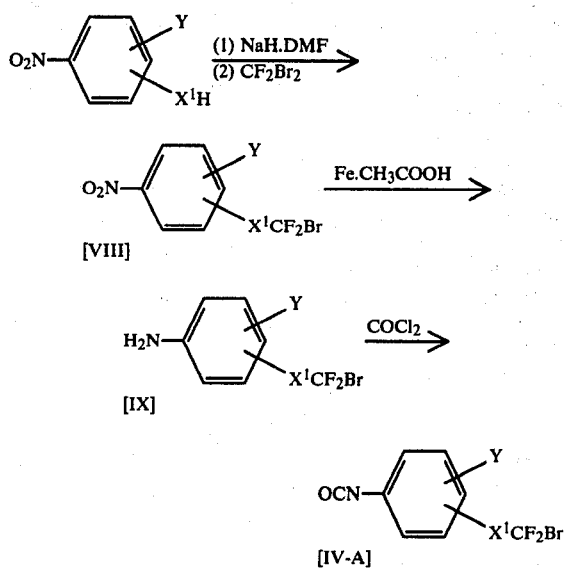

wherein Y and $X^1$ are defined above.

The compound having the formula [VIII] is easily produced by reacting NaH with nitrothiophenol or nitrophenol followed by the reaction of dibromodifluoromethane. The resulting product is reduced with iron powder and acetic acid to produce the aniline derivative having the formula [IX]. The isocyanate having the formula [IV-A] is produced by reacting phosgen with the product.

The typical pyrazoline derivatives of the present invention will be described in Tables 1.

TABLE 1

| No. | $R^1$ | $R^2$ | Y | $XR^3$ | Melting point (°C.) |
|---|---|---|---|---|---|
| 1 | ⟨phenyl⟩ | H | H | 4-$SCF_3$ | 166–168 |
| 2 | ⟨phenyl⟩ | H | H | 4-$SCF_2Cl$ | 149–151 |
| 3 | ⟨phenyl⟩ | H | H | 4-$SCF_2Br$ | 133–136 |
| 4 | ⟨phenyl⟩ | H | H | 4-$SCF_2H$ | 123–125 |
| 5 | ⟨phenyl⟩ | H | H | 4-$SOCF_3$ | 147–157 |
| 6 | ⟨phenyl⟩ | H | H | 4-$SOCF_2Cl$ | 140–147 |
| 7 | ⟨phenyl⟩ | H | H | 4-$SOCF_2Br$ |  |
| 8 | ⟨phenyl⟩ | H | H | 4-$SO_2CF_3$ | 135–138 |
| 9 | ⟨phenyl⟩ | H | H | 4-$SO_2CF_2Cl$ | 144–148 |
| 10 | ⟨phenyl⟩ | H | H | 4-$SO_2CF_2Br$ | 159–162 |
| 11 | ⟨phenyl⟩ | H | H | 4-$OCF_3$ | 125–126 |
| 12 | ⟨phenyl⟩ | H | H | 4-$OCF_2Br$ | 136–138 |
| 13 | ⟨phenyl⟩ | H | H | 4-$OCF_2Cl$ |  |
| 14 | ⟨phenyl⟩ | H | H | 4-$OCF_2H$ | 120–122 |

TABLE 1-continued $$\text{CF}_2\text{HO}-\underset{\underset{\underset{O=C-NH}{|}}{N}}{\overset{\overset{C-CH-R^1}{||}}{C}}\underset{C}{\overset{R^2}{\underset{R^2}{|}}}\overset{Y}{\underset{X-R^3}{\bigcirc}}$$

| No. | R¹ | R² | Y | XR³ | Melting point (°C.) |
|---|---|---|---|---|---|
| 15 | phenyl | H | 3-Cl | 4-OCF₂H | 118.5–121 |
| 16 | phenyl | H | 4-Cl | 3-OCF₂H | 112–117 |
| 17 | phenyl | H | H | 3-OCH₂CF₃ | 154–156 |
| 18 | phenyl | H | H | 4-OCH₂CF₃ | 165.5–167.5 |
| 19 | phenyl | H | H | 4-OCF₂CF₂H | 132–135 |
| 20 | phenyl | H | H | 4-OCF₂CFHCl | |
| 21 | phenyl | CH₃ | H | 4-SCF₃ | 139.5–141 |
| 22 | phenyl | CH₃ | H | 4-OCF₃ | 57–60 |
| 23 | 4-Cl-phenyl | H | H | 4-SCF₃ | 114–117 |
| 24 | 4-Cl-phenyl | H | H | 4-SCF₂Cl | 112–116 |
| 25 | 4-Cl-phenyl | H | H | 4-SO₂CF₂Cl | 168–171 |
| 26 | 4-Cl-phenyl | H | H | 4-OCF₃ | 117–119 |
| 27 | 4-Cl-phenyl | H | H | 4-OCF₂CF₂H | |
| 28 | 4-F-phenyl | H | H | 4-SCF₃ | 117–120 |
| 29 | 4-F-phenyl | H | H | 4-SCF₂Br | 115–119 |
| 30 | 4-F-phenyl | H | H | 4-SO₂CF₃ | 119–124 |
| 31 | 4-F-phenyl | H | H | 4-OCF₃ | 132–134 |
| 32 | 4-F-phenyl | H | H | 4-OCF₂Br | 121.5–123.5 |
| 33 | 4-F-phenyl | CH₃ | H | 4-OCF₂H | |
| 34 | H | H | H | 4-SCF₃ | 152.5–153.5 |
| 35 | H | H | H | 4-SCF₂Cl | 139–140 |
| 36 | H | H | H | 4-OCF₃ | 100–102 |
| 37 | H | H | H | 4-OCF₂CF₂H | 101–103 |
| 38 | CH₃ | H | H | 4-SCF₃ | 144–146 |
| 39 | CH₃ | H | H | 4-SCF₂Cl | 143–146 |
| 40 | CH₃ | H | H | 4-OCF₃ | 108–111 |
| 41 | CH₃ | H | H | 4-OCF₂Br | 96–97 |
| 42 | CH₃ | H | H | 4-OCF₂CF₂H | 124–129 |
| 43 | i-Pro | H | H | 4-SCF₃ | 104–108 |
| 44 | i-Pro | H | H | 4-SCF₂Cl | 57–59 |
| 45 | i-Pro | H | H | 4-OCF₃ | 103–107 |
| 46 | i-Pro | H | H | 4-OCF₂CF₂H | 86–88 |
| 47 | (CH₂)₃CN | H | H | 4-SCF₃ | 137.5–139 |
| 48 | (CH₂)₃CN | H | H | 4-SO₂CF₃ | 166–168 |
| 49 | (CH₂)₂OCH₃ | H | H | 4-SCF₂Cl | |
| 50 | (CH₂)₂OCH₃ | H | H | 4-OCF₂CF₂H | |
| 51 | (CH₂)₃OCH₃ | H | H | 4-OCF₃ | Oil ($N_D^{20}$ 1.5450) |
| 52 | (CH₂)₅CH₃ | H | H | 4-SCF₂Cl | 81–85 |
| 53 | (CH₂)₅CH₃ | H | H | 4-OCF₂CF₂H | 108–111 |

Certain compounds of the present invention include optical isomers having asymmetric carbon atom at 4-position of 2-pyrazoline ring. These isomers are also included in the compounds of the present invention.

The serial numbers of the compounds described in Table 1 are referred in the following Preparations, Compositions and Tests.

The compounds of the present invention are useful as insecticides for controlling insect pests in sanitation, and various insect pests in agriculture and horticulture which cause damages to rice, vegetable, fruits, cotton, and other crop plants and flowers and insect pests in forest and insect pests in storages, or insect pests expect agriculture and horticulture, for example termites.

The typical insect pests which are controlled by the compounds of the present invention are provided for purposes of illustration only.

Orthoptera

German Cockroach (*Blattella germanica*)
Rice Grasshopper (*Oxya yezoensis*)

Thysanoptera

Rice Thrips (*Baliothrips biformis*)

Hemiptera

Rice Stink Bug (*Lagynotomus elongatus*)
Green Stink Bug (*Nezcra antennata*)

Rice Bug (*Leptocorisa chinensis*)
Bean Bug (*Riotortus clavatus*)
Cotton Bug (*Dysdercus cingulatus*)
Gvape Leafhopper (*Epicanthus stramineus*)
Green Rice Leafhopper (*Nephotettix cincticeps*)
Small Brown Planthopper (*Laodelphax striatellus*)
Brown Rice Planthopper (*Nilaparvata lugens*)
White-backed Rice Planthopper (*Sogatella furcifera*)
Citrus Psylla (*Diaphorina citri*)
Greenhouse Whitefly (*Trialeurodes vaporariorum*)
Cowpea Aphid (*Aphis craccivora*)
Cotton Aphid (*Aphis gossypii*)
Apple Aphid (*Aphis spiraecola*)
Green Peach Aphid (*Myzue persicae*)
Citrus Mealybug (*Planococcus citri*)
Comstock Mealybug (*Pseudcoccus censtocki*)
Red Scale (*Aonidiella aurantri*)
San Jose Scale (*Comstockaspis perniciosa*)
Arrowhead Scale (*Unaspis yanonensis*)

Lepidoptera

Apple Leafminer (*Phyllonorycfer ringoneella*)
Citrus Leafminer (*Phyllocnistis citrella*)
Diamondback Moth (*Plutella xylostella*)
Pink Bollworm (*Pectinophora gossypiella*)
Potato Tuberworm (*Phthorimaea operculella*)
Peach Fruit Moth (*Carposina niponensis*)
Summer Fruit Tortrix (*Adoxophyes orana*)
Oriental Fruit Moth (*Grapholita molesta*)
Soybean Pod Borer (*Leguminivora glycinivorella*)
Rice Stem Borer (*Chilo suppressalis*)
Rice Leafroller (*Chaphalocrocis medinalis*)
Pea Pod Borer (*Etiella zinckenella*)
Oriental Corn Borer (*Ostrinia furnacalis*)
Yellow Rice Borer (*Tryporyza incertulas*)
Cutworm (*Agrotis segetum*)
Cotton Looper (*Anomis flava*)
American Bollworm, Cotton Bollworm or Tabacco Budworm (*Heliothis armigera, H. zea H. virescens*)
Cabbage armyworm (*Mamestra brassicae*)
Beet Semi Looper (*Plusia nigrisigna*)
Rice Armyworm (*Pseudaletia separata*)
Pink Borer (*Sesamia inferens*)
Common Cutworm (*Spodoptcra litura*)
Common White (*Pieris rapae crucivora*)
Smaller Citrus Dog (*Papilio xuthus*)
Rice Skipper (*Parnara guttata*)
Codling Moth (*Cydia pomonella*)

Coleoptera

Cupreous Chafer (*Anomala cuprea*)
Asiatic Garden Beetle (*Maladera castanea*)
Japanese Beetle (*Popillia Japonica*)
Twenty-eight-spotted Ladybeetle (*Henosepilachna vignitioctopunctata*)
Cucurbit Leaf Beetle (*Aulacophora femoralis*)
Rice Leaf Beetle (*Oulema oryaze*)
Striped Flea Beetle (*Phyllotreta striolata*)
Rice Plant Weevil (*Echinocnemus squameus*)
Rice Water Weevil (*Lissorhoptrus oryzophilus*)
Vegetable Weevil (*Listroderes obliquus*)
Maize Weevil (*Sitophilus zeamais*)
Bull Weevil (*Anthonomus grandis*)
Corn Rootworms (Diabrotica spp.)
Colorado Potato Beetle (*Leptinotarsa decemlineata*)

Hymenoptera

Fire Ant (*Solenopsis geminata*)

Diptera

Soybean Pud Gall Midge (Asphondylia spp.)
Oriental Fruit Fly (*Dacus dorsalis*)
Rice Leafminer (*Hydrellia griseola*)
Rice Stem Maggot (*Chlorops oryzae*)
Rice Leafminer (*Agromyza oryzae*)
Seedcorn Maggot (*Hylemya platura*)
Mediterranean Fruit Fly (*Ceratitis capitata*)
Rice Gall Midge (*Orseolia oryzae*)
House Fly (*Musca domestica*)
Pale House Mosquito (*Culex pipiens pallens*)

The insecticidal activity of the compounds of the present invention is imparted not only young larva but also old larva in direct or in penetration by direct contact or immersion. The compounds of the present invention are also effective to control various acarina and nematode.

In the application of the insecticidal composition of the present invention, it is preferable to apply it at a concentration of 0.01 to 10,000 ppm preferably 0.1 to 2,000 ppm of the active ingredient. In order to control aquatic insect pests, the composition having said concentration can be sprayed to the part to control the aquatic insect pests. Therefore, the concentration of the active ingredient in water can be lower.

In the application of the compound of the present invention as the insecticide, it is preferable to prepare a composition by mixing the active ingredient with a desired solid carrier such as clay, talc and bentonite; or a liquid carrier such as water, alcohols (methanol, ethanol etc.), ketones, ethers, aliphatic hydrocarbons, aromatic hydrocarbons (benzene, toluene, xylene etc.), esters and nitriles, if necessary, with an emulsifier, a dispersing agent, a suspending agent, a spreader, a penetrant and a stabilizer so as to form suitable compositions for practical applications in the form of an emulsifiable concentrate, an oil spray, a wettable powder, a dust, a granule, a tablet, a paste, a flowable, a bait poison, an aerosol, a fumigrant, a mosquito-coil and electric mosquito mat.

It is possible to blend the active ingredient of the present invention to a suitable other active ingredient such as the other insecticides, germicides, herbicides, plant growth regulators, and fertilizers in the preparation of the composition or in the application.

The present invention will be further illustrated by certain examples of Preparations, Compositions and Tests which are provided for purposes of illustration only and are not intended to be limiting the present invention.

Preparation 1

1-(4-Trifluoromethylthiophenylcarbamoyl)-3-(4-difluoromethoxyphenyl)-4-phenyl-2-pyrazoline Preparation of Compound No. 1

(a) Preparation of 3-(4-difluoromethoxyphenyl)-4-phenyl-2-pyrazoline(Intermediate)

A mixture of 17 g. of 4'-hydroxy-2-phenylacetophenone and 30 g. of sodium hydroxide in 40 ml. of water and 50 ml. of dioxane was heated at 70° to 80° C. and 22 g. of Freon 22 gas was fed into the solution during 1 hour while heating. After cooling the reaction mixture, 150 ml. of water and 150 ml. of ethyl ether were added to the reaction mixture and an organic phase was obtained by an extraction. The organic phase was separated and dried over anhydrous sodium sulfate and ethyl ether was distilled off to obtain 17.6 g. of 4'-difluoromethoxy-2-phenylacetophenone (melting point of 39.0°–40.0° C.). Into a mixture of 0.9 ml. of piperidine, 0.9 ml. of acetic acid, 25 ml. of 37% formaline and 180 ml. of methanol, 17.5 g. of the resulting compound was added and the mixture was refluxed for 3 hours to react them. The reaction mixture was concentrated under a reduced pressure and 150 ml. of water and 200 ml. of chloroform were added. The resulting organic phase was separated and dried over anhydrous sodium sulfate and chloroform was distilled off to obtain 18.0 g. of 4'-difluoromethoxy-2-phenylacrylophenone ($N_D^{20}$ 1.5819). A mixture of 17.5 g. of the product, 8 ml. of hydrazine hydrate and 150 ml. of ethanol was refluxed for 3 hours to react them. After the reaction, the reaction mixture was concentrated under a reduced pressure and 80 ml. of water and 100 ml. of chloroform were added. The resulting organic phase was separated and dried over anhydrous sodium sulfate and chloroform was distilled off to obtain 17.5 g. of 3-(4-difluoromethoxyphenyl)-4-phenyl-2-pyrazoline (melting point of 65°–75° C.).

(b) Preparation of Compound No. 1

Into 20 ml. of anhydrous ethyl ether, 5.8 g. of 3-(4-difluoromethoxyphenyl)-4-phenyl-2-pyrazoline obtained in the step (a) and 4.4 g. of 4-trifluoromethylthiophenylisocyanate were charged and the mixture was refluxed for 6 hours to react them. After cooling, the precipitated crystal (6.2 g.) was separated by a filtration. It was confirmed that the product was 1-(4-trifluoromethylthiophenyl-carbamoyl)-3-(4-difluoromethoxyphenyl)-4-phenyl-2-pyrazoline (melting point of 166°–168° C.) by the NMR spectrum (I).

Preparation 2

1-(4-Trifluoromethylsulfinylphenylcarbamoyl)-3-(4-difluoromethoxyphenyl)-4-phenyl-2-pyrazoline Preparation of Compound No. 5

Into 20 ml. of acetic acid, 0.74 g. of 1-(4-trifluoromethylthiophenylcarbamoyl)-3-(4-difluoromethoxyphenyl)-4-phenyl-2-pyrazoline obtained by the process of Preparation 1 was charged and 0.2 ml. of 30% $H_2O_2$ was charged. The mixture was stirred for 24 hours at room temperature and then, 0.2 ml. of 30% $H_2O_2$ was further charged and the mixture was stirred for 72 hours. Into the reaction mixture, 60 ml. of water was added and the product was extracted tow times with 60 ml. of chloroform. The chloroform layer was dried over anhydrous magnesium sulfate. Chloroform was distilled off under a reduced pressure. The residue was admixed with 40 ml. of n-hexane-ethyl ether (1:1) and the precipitated crystal was separated by a filtration. The yield was 0.5 g.

It was confirmed that the product was 1-(4-trifluoromethylsulfinylphenylcarbamoyl)-3-(4-difluoromethoxyphenyl)-4-phenyl-2-pyrazoline (melting point of 147°–157° C.) by the NMR spectrum (II).

Preparation 3

1-(4-Bromodifluoromethylthiophenylcarbamoyl)-3-(4-difluoromethoxyphenyl)-4-phenyl-2-pyrazoline Preparation of Compound No. 3

(a) Preparation of p-bromodifluoromethylthiophenylisocyanate

On an ice bath, NaH (50%, 8.0 g. 167 m mol) was suspended in dimethylformamide (150 ml.) and a solution of p-nitrothiophenol (25 g, 161 m mol) in dimethylformamide (200 ml.) was added and the mixture was stirred for 30 minutes on the ice bath. A solution of dibromodifluoromethane (50 g. 238 m mol) in dimethylformamide (100 ml.) was added and the mixture was stirred for 1 hour on the ice bath and further stirred for 5 hours at room temperature. Water was added to the reaction mixture and the product was extracted with methylene chloride, and dried over anhydrous magnesium sulfate. A crude product obtained by concentrating the extract, was purified by a column chromatography to obtain 40.4 g. of p-(bromodifluoromethylthio)nitrobenzene (melting poing of 72°–73° C.). The yield was 88%.

Into ethanol (300 ml.), the resulting p-(bromodifluoromethylthio) nitrobenzene (32.4 g.), iron powder (25 g.) and acetic acid (60 ml.) were added. The mixture was refluxed for 1 hour. After removing most of the solvent under a reduced pressure, water was added and the product was extracted with ether. The extract was washed with NaCl aq. soln. and dried over anhydrous magnesium sulfate. After removing the solvent, the product was purified by a column chromatography to obtain 15.5 g. of p-(bromodifluorometylthio) aniline. The yield was 54%.

A solution of p-(bromodifluoromethylthio) aniline (4 g.) in 40 ml. of ethyl acetate was added dropwise while feeding phosgen. After the addition, phosgen was further fed for 10 minutes. The reaction mixture was concentrated under a reduced pressure to obtain 4 g. of the product ($N_D^{20}$ 1.5790). The product was used without any purification as a reagent in the next reaction.

(b) Preparation of Compound No. 3

Into 50 ml. of anhydrous ethyl ether, 5.6 g. of p-bromodifluoromethylthiophenylisocyanate obtained in the step (a) and 5.8 g. of 3-(4-difluoromethoxyphenyl)-4-phenyl-2-pyrazoline obtained in the step (a) of Preparation 1 were charged and the mixture was stirred for 6 hours at room temperature. The precipitated crystal was separated by a filtration and washed with n-hexane. The yield was 5.8 g.

It was confirmed that the product was 1-(4-bromodifluoromethylthiophenylcarbamoyl)-3-(4-difluoromethoxyphenyl)-4-phenyl-2-pyrazoline (melting point of 133°–136° C.) by the NMR spectrum (III).

Preparation 4

1-(4-Bromodifluoromethylsulfonylphenylcarbamoyl)-3-(4-difluoromethoxyphenyl)-4-phenyl-2-pyrazoline Preparation of Compound No. 10

Into 40 ml. of acetic acid, 4 g. of 1-(4-bromodifluoromethylthiophenylcarbamoyl)-3-(4-difluoromethoxyphenyl)-4-phenyl-2-pyrazoline obtained in Preparation 3 was dissolved and 80 ml. of 30% $H_2O_2$ was added and the mixture was heated at 60° C. After 4 hours, water was added to the reaction mixture. The product was extracted two times with 50 ml. of chloroform. The chloroform layer was washed with 50 ml. of NaHCO$_3$ aq. soln. and dried over anhydrous sodium sulfate. The solvent was distilled off under a reduced prssure to obtain 3.8 g. of the crude product. The product was recrystallized by using 20 ml. of n-hexane-ether (1:1) to obtain 2.2 g. of the product.

It was confirmed that the product was 1-(4-bromodifluoromethylsulfonylphenylcarbamoyl)-3-(4-difluoromethoxyphenyl)-4-phenyl-2-pyrazoline (melting point of 159°–162° C.) by the NMR spectrum (IV).

Preparation 5

1-(4-Bromodifluoromethoxyphenylcarbamoyl)-3-(4-difluoromethoxyphenyl)-4-(4-fluorophenyl)-2-pyrazoline Preparation of Compound No. 32

(a) Preparation of 3-(4-difluoromethoxyphenyl)-4-(4-fluorophenyl)-2-pyrazoline

In accordance with the process (a) of Preparation 1 except using 18.4 g. of 4'-hydroxy-2-(4-fluorophenyl)-acetophenone instead of 4'-hydroxy-2-phenyl-acetophenone, 4'-difluoromethoxy-2-(4-fluorophenyl)-acetophenone (melting point of 50°–56° C.) as an intermediate was obtained. Then, 4'-difluoromethoxy-2-(4-fluorophenyl)acrylophenone (N$_D^{20}$ 1.5594) was produced by reacting formaline with the product.

Then, 15.2 g of 3-(4-difluoromethoxyphenyl)-4-(4-fluorophenyl)-2-pyrazoline was produced by reacting hydrazine hydrate with the product. The reaction mixture was used as a reagent in the following step (c) without any purification.

(b) Preparation of p-bromodifluoromethoxyphenylisocyanate

Into DMF (20 ml.), 50% NaH (5.0 g. 104 m mol) was added and the mixture was cooled on an ice bath. A solution of p-nitrophenol (13.9 g. 100 m mol) in DMF (100 ml.) was added dropwise and the mixture was stirred for 10 minutes. A solution of dibromodifluoromethane (25 g. 119 m mol) in DMF (60 ml.) was added and the mixture was stirred for 5 hours at room temperature. The reaction mixture was poured into water and the product was extracted with ether. The ether layer was dried over anhydrous magnesium sulfate and the solvent was distilled off and the product was distilled to obtain 13.4 g. of p-nitro(bromodifluoromethoxy)benzene (boiling point of 74°–77° C./0.1 mmHg). The yield was 50%.

Into ethanol (100 ml.), the resulting p-(bromodifluoromethoxy)nitrobenzene (10.0 g.), iron powder (7.5 g.) and acetic acid (16 g.) were added. The mixture was refluxed for 2 hours. After distilling off most of ethanol, water was added and the product was extracted with ether. The ether layer was washed with NaCl aq. soln. and dried over anhydrous magnesium sulfate. The solvent was removed and the product was distilled to obtain 6.2 g. of p-(bromodifluoromethoxy)aniline (boiling point of 65°–72° C./0.1 mmHg). The yield was 70%.

Into 40 ml. of ethyl acetate, 4 g. of p-(bromodifluoromethoxy)aniline was dissolved. The solution was added dropwise to 40 ml. of ethyl acetate while feeding phosgen. After the addition, phosgen was further fed for 10 min. The reaction mixture was concentrated under a reduced pressure to obtain 4 g. of the product (N$_D^{20}$ 1.4903).

The product was used as a reagent in the next step without any purification.

(c) Preparation of Compound No. 32

Into 20 ml. of anhydrous ethyl ether, 6.1 g. of 3-(4-difluoromethoxyphenyl)-4-(4-fluorophenyl)-2-pyrazoline obtained in the step (a) and 5.3 g. of p-bromodifluoromethoxyphenylisocyanate obtained in the step (b) were charged to react them as the step (b) of Preparation 3. to obtain 7.1 g. of 1-(4-bromodifluoromethoxyphenylcarbamoyl)-3-(4-difluoromethoxyphenyl)-4-(4-fluorophenyl)-2-pyrazoline (melting point of 121.5°–123.5° C.).

The formula of the product was confirmed by the NMR spectrum (V).

Preparation 6

1-(4-Trifluoromethoxyphenylcarbamoyl)-3-(4-difluoromethoxyphenyl)-4-(4-chlorophenyl)-2-pyrazoline Preparation of Compound No. 26

(a) Preparation of 3-(4-difluoromethoxyphenyl)-4-(4-chlorophenyl)-2-pyrazoline(Intermediate)

In accordance with the process of step (a) of Preparation 1, 4'-difluoromethoxy-2-(4-chlorophenyl)-acetophenone (melting point 74.0°–76.0° C.) was produced as an intermediate by using 20 g. of 4'-hydroxy-2-(4-chlorophenyl)-acetophenone instead of 4'-hydroxy-2-phenyl-acetophenone. Then, 4'-difluoromethoxy-2-(4-chlorophenyl) acrylophenone (N$_D^{20.5}$ 1.5752) was obtained by reacting the intermediate with formaline. Then, a reaction of hydrazine hydrate with the product was carried out to obtain 11.6 g. of 3-(4-difluoromethoxyphenyl)-4-(4-chlorophenyl)-2-pyrazoline. The product was used as the intermediate for the next step without a purification.

(b) Preparation of Compound No. 26

Into 20 ml. of anhydrous ethyl ether, 6.5 g. of 3-(4-difluoromethoxyphenyl)-4-(4-chlorophenyl)-2-pyrazoline obtained in the step (a) and 4.0 g. of 4-trifluoromethoxyphenylisocyanate were added and the mixture was kept at room temperature for one night and the precipitated crystal (6.3 g.) was separated by a filtration. It was confirmed that the product was 1-(4-trifluoromethoxyphenylcarbamoyl)-3-(4-difluoromethoxyphenyl)-4-(4-chlorophenyl)-2-pyrazoline (melting point of 117°–119° C.) by the NMR spectrum (VI).

Preparation 7

1-(4-Trifluoromethylthiophenylcarbamoyl)-3-(4-difluoromethoxyphenyl)-4-phenyl-5,5-dimethyl-2-pyrazoline Preparation of Compound No. 21

(a) Preparation of 3-(4-difluoromethoxyphenyl)-4-phenyl-5,5-dimethyl-2-pyrazoline Into a solution of 43 g. of 4'-difluoromethoxy-2-phenyl acetophenone obtained in the process (a) of Preparation 1 in 200 ml. of anhydrous tetrahydrofuran was cooled on an ice bath and 10 g. of NaH (55% in mineral oil) was added, and the mixture was stirred for 10 min.

and then, 30 g. of isopropyl iodide was added dropwise. After the addition, the mixture was refluxed for 4 hours.

After the reaction, tetrahydrofuran distilled off and 200 ml. of water and 200 ml. of ether were added to separate the organic phase by extraction. The water phase was treated with 100 ml. of ether by the extraction. The organic phases were mixed and dried over anhydrous sodium sulfate and the solvent was distilled off and the product was purified by a column chromatography (silica gel: benzene) to obtain 44 g. of 4'-difluoromethoxy-2-phenylisovalerophenone ($N_D^{20}$ = 1.5312). Into 20 ml. of carbon tetrachloride, 2.9 g. of the resulting product was dissolved and then, 0.54 ml. of bromine was added dropwise at room temperature and the mixture was stirred at room temperature for 24 hours. The reaction mixture was concentrated under a reduced pressure and 20 ml. of dimethylformamide was added to form a solution and 1.73 g. of LiCl was added and the mixture was heated at 130° C. for 3 hours. Into the reaction mixture, 50 ml. of water and 50 ml. of ethyl ether were added and the organic phase was separated by a phase separation and was dried over anhydrous sodium sulfate, and ethyl ether was distilled off to obtain 2.7 g. of 4'-difluoromethoxy-α-phenyl-β,β-dimethyl acrylophenone ($N_D^{20}$ = 1.5623).

Into 20 ml. of methanol, 1.0 g. of the product and 1.7 ml. of hydrazine hydrate were dissolved. The reactor was wrapped with aluminum foil to be dark. The mixture was stirred at room temperature in nitrogen atmosphere for 24 hours. The reaction mixture was concentrated under a reduced pressure and 20 ml. of ethyl ether and 20 ml. of water were added. The organic phase was dried over anhydrous sodium sulfate and ethyl ether was distilled off to obtain 1.0 g. of the crude product. The product was used in the next step without any purification.

(b) Preparation of Compound No. 21

Into 20 ml. of anhydrous ethyl ether, 1.0 g. of the crude product obtained in the step (a) and 0.77 g. of 4-trifluoromethylthiophenylisocyanate were charged to react them at room temperature for 24 hours. The precipitated by-product of N,N'-bis(4-trifluoromethylthiophenyl)urea was separated by a filtration and ethyl ether was distilled off under a reduced pressure to obtain 1.5 g. of the crude product. The crude product was admixed with 20 ml. of n-hexaneethyl ether (1:1) and the precipitated crystals was separated by a filtration. The yield was 0.7 g.

It was confirmed that the product is 1-(4-trifluoromethylthiophenylcarbamoyl)-3-(4-difluoromethoxyphenyl)-4-phenyl-5,5-dimethyl-2-pyrazoline (melting point of 139.5°-141° C.) by the NMR spectrum (VII).

Preparation 8

1-(4-1',1',2',2'-Tetrafluoroethoxyphenylcarbamoyl)-3-(4-difluoromethoxyphenyl)-2-pyrazoline Preparation of Compound No. 37

(a) Preparation of 3-(4-difluoromethoxyphenyl)-2-pyrazoline (Intermediate)

In a reactor A, 54.4 g. of 4-hydroxyacetophenone was added to a solution of 17 g. of sodium hydroxide in 160 ml. of water and 400 ml. of dioxane.

On the other hand, in a reactor B, a solution of 80 g. of sodium hydroxide in 300 ml. of water and 360 ml. of dioxane was prepared. The reactor B was heated to 80° C. and Freon 22 gas was fed and the resulting difluorocarbene was fed through a polytetrafluoroethylene tube into the reactor A at room temperature. After feeding 200 g. of Freon 22 gas, the reactor A was cooled and 400 ml. of water and 500 ml. of ethyl ether were charged for an extraction. The resulting organic phase was separated and dried over anhydrous sodium sulfate and ethyl ether was distilled off to obtain a crude product. The crude product was distilled under a reduced pressure to obtain 44.6 g. of 4-difluoromethoxyacetophenone having a boiling point of 98°-100° C./3 mmHg. A mixture of 44 g. of the resulting product, 19.3 g. of dimethylamine hydrochloride, 7.3 g. of paraformaldehyde and 30 ml. of ethanol and 3 ml. of conc. hydrochloric acid was refluxed for 3 hours to react them. The solvent was distilled off under a reduced pressure and the crystal as the residue was obtained. The residue was mixed with 18 ml. of acetone and the crystal was separated by a filtration to obtain 4'-difluoromethoxy-3-dimethylaminopropiophenone hydrochloride having a melting point of 135.0°-140° C.

A mixture of the resulting crystal, 150 ml. of methanol. 33 ml. of hydrazine hydrate, 17 ml. of 50% NaOH aq. soln. and 45 ml. of water was refluxed for 1 hour. Methanol was distilled off and then, dichloromethane and water were added for an extraction. The resulting organic phase was separated and dried over anhydrous sodium sulfate and dichloromethane was distilled off to obtain 32 g. of 3-(4-difluoromethoxyphenyl)-2-pyrazoline. The product was used as the intermediate in the next reaction step without any purification.

(b) Preparation of Compound No. 37

Into 30 ml. of anhydrous ethyl ether, 4.2 g. of 3-(4-difluoromethoxyphenyl)-2-pyrazoline obtained in the step (a) and 9.4 g. of 4,1',1'2',2'-tetrafluoroethoxyphenylisocyanate were charged and the mixture was kept at room temperature for one night and the precipitated crystal (9.5 g.) was separated by a filtration.

It was confirmed that the product was 1-(4-1',1',2',2'-tetrafluoroethoxyphenylcarbamoyl)-3-(4-difluoromethoxyphenyl)-2-pyrazoline (melting point of 101°-103° C.) by the NMR spectrum (VIII).

Preparation 9

1-(4-Chlorodifluoromethylthiophenylcarbamoyl)-3-(4-difluoromethoxyphenyl)-4-methyl-2-pyrazoline Preparation of Compound No. 39

(a) Preparation of 3-(4-difluoromethoxyphenyl)-4-methyl-2-pyrazoline (Intermediate)

In accordance with the process of Preparation 8, 4-difluoromethoxy propiophenone (boiling point of 108°-109° C. mmHg) was produced as an intermediate by using 60 g. of 4-hydroxypropiophenone instead of 4-hydroxyacetophenone. Then, the product was dimethylaminomethylated to obtain 4'-difluoromethoxy-3-dimethylamino-2-methylpropiophenone hydrochloride (melting point of 134.0°-136.0° C.). Then, a reaction of hydrazine hydrate with the product in the presence of 50% NaOH aq. soln. was carried out to obtain 37 g. of 3-(4-difluoromethoxyphenyl)-4-methyl-2-pyrazoline. The product was used as the intermediate for the next step without a purification.

(b) Preparation of Compound No. 39

Into 20 ml. of anhydrous ethyl ether, 4.7 g. of 3-(4-difluoromethoxyphenyl)-4-methyl-2-pyrazoline obtained in the step (a) and 4.7 g. of 4-chlorodifluoromethylthiophenylisocyanate were added and the mixture was kept at room temperature for one night and then ethyl ether was distilled off under a reduced pressure to obtain a crude product. The crude product was purified by a silica gel thin layer chromatography (developing solvent:benzene:ethyl acetate=4:1) to obtain 5.6 g. of the product in the crystalline form.

It was confirmed that the product was 1-(4-chlorodifluoromethylthiophenylcarbamoyl)-3-(4-difluoromethoxyphenyl)-4-methyl-2-pyrazoline (melting point of 143°–146° C.) by the NMR spectrum (IX).

Preparation 10

1-(4-Trifluoromethoxyphenylcarbamoyl)-3-(4-difluoromethoxyphenyl)-4-isopropyl-2-pyrazoline

Preparation of Compound No. 45

(a) Preparation of 3-(4-difluoromethoxyphenyl)-4-isopropyl-2-pyrazoline

In accordance with the process of Preparation 8 except using 71.2 g. of 4-hydroxyisovalerophenone instead of 4-hydroxyacetophenone, 4-difluoromethoxyisovalerophenone (boiling point of 108°–110° C./0.5 mmHg) as an intermediate was obtained. The product was dimethylaminomethylated to obtain 4'-difluoromethoxy-3-dimethylamino-2-isopropylpropiophenone hydrochloride. The product was reacted with hydrazine hydrate in the presence of 50% NaOH aq. soln. to obtain 43 g. of 3-(4-difluoromethoxyphenyl)-4-isopropyl-2-pyrazoline. The product was used in the next step without any purification.

(b) Preparation of Compound No. 45

Into 3 ml. of anhydrous ethyl ether, 5.1 g. of 3-(4-difluoromethoxyphenyl)-4-isopropyl-2-pyrazoline and 4.0 g. of 4-trifluoromethoxyphenylisocyanate were charged and the mixture was kept at room temperature for one night and ethyl ether was distilled off under a reduced pressure to obtain a crude product.

The crude product was purified by a silica gel thin layer chromatography (benzene:ethyl acetate=4:1 as developer) to obtain 4.5 g. of a crystalline product.

It was confirmed that the product is 1-(4-trifluoromethoxyphenylcarbamoyl)-3-(4-difluoromethoxyphenyl)-4-isopropyl-2-pyrazoline (melting point of 103°–107° C.) by the NMR spectrum (X).

Preparation 11

1-(4-Trifluoromethylthiophenylcarbamoyl)-3-(4-difluoromethoxyphenyl)-4-(3-cyanopropyl)-2-pyrazoline

Preparation of Compound No. 47

(a) Preparation of 3-(4-difluoromethoxyphenyl)-4-(3-cyanopropyl)-2-pyrazoline

Into a solution of 17 g. of NaOH in 160 ml. of water and 400 ml. of dioxane, 79.4 g. of 4'-hydroxy-5-chlorovalerophenone was added in Reactor A.

On the other hand, a solution of 80 g. of NaOH in 300 ml. of water and 360 ml. of dioxane was prepared in Reactor B. The Reactor B was heated at 80° C., Freon-22 gas was fed and the resulting difluorocarbene was fed through a polytetrafluoroethylene tube (previously connected) into the Reactor A. In the Reactor A, the temperature was raised. After feeding 200 g. of Freon-22, the Reactor A was cooled and 400 ml. of water and 500 ml. of ethyl ether were charged to separate an organic phase by extraction. The organic phase was dried over anhydrous sodium sulfate and ethyl ether was distilled off as a crude product of 4'-difluoromethoxy-5-chlorovalerophenone.

Into 20 ml. of acetonitrile, 13 g. of the crude product was dissolved and 6.5 g. of potassium cyanide and 1 g. of 18-crown-6 were added to the solution and the mixture was refluxed for 3 hours. After cooling the reaction mixture, an insoluble matter was separated by a filtration and 50 ml. of water was added to the filtrate. The product was extracted two times with 50 ml. of chloroform and the chloroform phase was dried over anhydrous sodium sulfate and the solvent was distilled off under a reduced pressure to obtain 12 g. of the crude product. The crude product was purified by a column chromatography (silica gel:ethyl acetate:benzene=1:9 as developer) to obtain 9 g. of 4'-difluoromethoxy-5-cyanovalerophenone ($N_D^{20}$ 1.5045). The product (4.8 g.) was admixed with 2 g. of dimethylamine hydrochloride, 0.8 g. of paraformaldehyde and 20 ml. of dioxane and the mixture was refluxed for 24 hours. After distilling off dioxane, 30 ml. of water was added and the product was extracted two times with 30 ml. of ether. The ether phase was dried over anhydrous sodium sulfate and ether was distilled off to obtain 4.7 g. of 4''-difluoromethoxy-α-(3-cyanopropyl) acrylophenone.

The product was dissolved into 50 ml. of methanol and then 3 ml. of hydrazine hydrate was added and the mixture was refluxed for 3 hours. After distilling off methanol, 30 ml. of water was added and the product was extracted two times with 30 ml. of ether and the ether phase was dried over anhydrous sodium sulfate and ether was distilled off to obtain 4.8 g. of 3-(4-difluoromethoxyphenyl)4-(3-cyanopropyl)-2-pyrazoline. The product was used in the next step without any purification.

(b) Preparation of Compound No. 47

Into 20 ml. of anhydrous ethyl ether, 5.6 g. of 3-(4-difluoromethoxyphenyl)-4-(3-cyanopropyl)-2-pyrazoline obtained in the step (a) and 4.4 g. of 4-trifluoromethylthiophenylisocyanate were charged and the mixture was kept at room temperature for one night and ethyl ether was distilled off under a reduced pressure to obtain a crude product. The product was purified by a silica gel thin layer chromatography (benzeneethyl acetate=4:1) to obtain 4 g. of a crystalline product.

It was confirmed that the product is 1-(4-trifluoromethylthiophenylcarbamoyl)-3-(4-difluoromethoxyphenyl)-4-(3-cyanopropyl)-2-pyrazoline (melting point of 137.5°–139° C.) by the NMR spectrum (XI).

Preparation 12

1-(4-Trifluoromethoxyphenylcarbamoyl)-3-(4-difluoromethoxyphenyl)-4-(3-methoxypropyl)-2-pyrazoline

Preparation of Compound No. 51

(a) Preparation of 3-(4-difluoromethoxyphenyl)-4-(3-methoxypropyl)-2-pyrazoline

Into 20 ml. of methylalcohol, 6.0 g. of 4'-difluoromethoxy-5-chlorovalerophenone was dissolved and 1.2 g. of sodiummethoxide was added. The mixture was refluxed for 6 hours and was concentrated under reduced pressure and 50 ml. of water was added to the residue. The product was extracted with 50 ml. of ethyl ether and the ether layer was dried over anhydrous sodium sulfate and the solvent was distilled off to obtain 5.5 g. of the crude product. The crude product was purified by a column-chromatography (silica gel:benzene) to obtain 3.0 g. of 4'-difluoromethoxy-5-methoxyvalerophenone ($N_D^{20}$ 1.4950). The structure was confirmed by the NMR spectrum [CCl$_4$, δ, ppm; 1.50–1.90 (4H, m); 2.85 (2H, t, J=6.0 Hz); 3.20 (3H, S); 3.30 (2H, t, J=6.0 Hz); 6.53 (1H, t, J=73 Hz); 7.07 (2H, d, J=9.0 Hz); 7.87 (2H, d, J=9.0 Hz)].

The product (3.0 g.) was admixed with 1.3 g. of dimethylamine hydrochloride, 0.5 g. of paraformaldehyde, 1 ml. of 12N hydrochloric acid and 5 ml. of dioxane and the mixture was refluxed for 40 hours.

After distilling off dioxane, 20 ml. of water was added and the product was extracted two times with 30 ml. of ether. The ether layer was dried over anhydrous sodium sulfate and eher was distilled off to obtain 2.0 g. of 4'-difluoromethoxy-(α-3-methoxypropyl) acrylophenone.

The product (2.0 g) was dissolved into 50 ml. of ethylalcohol and then 1.5 ml. of hydrazine hydrate was added and the mixture was refluxed for 2 hours.

After distilling off ethylalcohol, 50 ml. of water was added and the product was extracted with 50 ml. of ethyl ether and the ether layer was dried over anhydrous sodium sulfate and ether was distilled off to obtain 2.0 g. of 3-(4-difluoromethoxyphenyl)-4-(3-methoxypropyl)-2-pyrazoline. The product was used in the next step without any purification.

(b) Preparation of Compound No. 51

Into 20 ml. of anhydrous ethylether, 2.0 g. of 3-(4-difluoromethoxyphenyl)-4-(3-methoxypropyl)-2-pyrazoline obtained in the step (a) and 1.2 g. of p-trifluoromethoxyphenylisocyanate were charged and the mixture was kept at room temperature for 18 hours and ethyl ether was distilled off under reduced pressure to obtain a crude product. The crude product was purified by a silica gel column chromatography (silica gel; benzene) to obtain 0.3 g. of the product.

It was confirmed that the product is 1-(4-trifluoromethoxyphenylcarbamoyl)-3-(4-difluoromethoxyphenyl)-4-(3-methoxypropyl)-2-pyrazoline by the NMR spectrum (XII) and by the Mass Spectrum.

Mass spectrum; m/Z 487(M+), 414(M+-(CH$_2$)$_3$OCH$_3$),

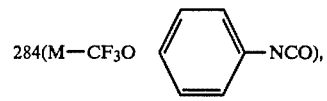

284(M—CF$_3$O—C$_6$H$_4$—NCO),

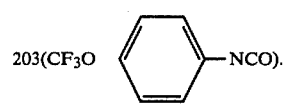

203(CF$_3$O—C$_6$H$_4$—NCO).

NMR spectra (I)–(XII)
$^1$H—NMR: δ(CDCl$_3$, TMS, ppm)

| NMR spectrum | |
|---|---|
| I | 3.90–4.90 (3H, m); 6.50 (1H, t, J = 73Hz); 7.30 (5H, s); 7.67 (4H, s); 7.00–7.80 (4H, m); 8.30 (1H, bs) |
| II | 3.90–4.95 (3H, m); 6.49 (1H, t, J = 73Hz); 7.29 (5H, s); 7.80 (4H, s); 6.90–7.85 (4H, m); 8.40 (1H, bs) |
| III | 3.90–4.90 (3H, m); 6.50 (1H, t, J = 73Hz); 7.30 (5H, s); 7.66 (4H, s); 6.95–7.85 (4H, m); 8.30 (1H, bs) |
| IV | 3.90–4.85 (3H, m); 6.53 (1H, t, 73Hz); 7.33 (5H, s); 7.00–7.85 (4H, m); 7.98 (4H, s); 8.60 (1H, bs) |
| V | 3.80–4.90 (3H, m); 6.53 (1H, t, J = 73Hz); 6.90–7.80 (12H, m); 8.20 (1H, bs) |
| VI | 3.80–4.90 (3H, m); 6.49 (1H, t, J = 73Hz); 6.90–7.80 (12H, m); 8.17 (1H, bs) |
| VII | 1.28 (3H, s); 1.63 (3H, s); 4.25 (1H, s); 6.48 (1H, t, J = 73Hz); 6.95–7.75 (13H, m); 8.43 (1H, bs) |
| VIII | 2.95–3.45 (2H, m); 3.85–4.30 (2H, m); 5.90 (1H, tt, J = 54.0Hz and 3.0Hz); 6.57 (1H, t, J = 73Hz); 7.00–7.90 (8H, m); 8.07 (1H, bs) |
| IX | 1.30 (3H, d, J = 6.0Hz); 3.45–4.25 (3H, m); 6.59 (1H, t, J = 73Hz); 7.19 (2H, d, J = 9.0Hz); 7.60 (4H, s); 7.78 (2H, d, J = 9.0Hz); 8.20 (1H, bs) |
| X | 0.72 (3H, d, J = 7.0Hz); 1.03 (3H, d, J = 7.0Hz); 2.10 (1H, m); 3.70–4.20 (3H, m); 6.59 (1H, t, J = 73Hz); 7.05–7.90 (8H m); 8.10 (1H, bs) |
| XI | 1.50–1.90 (4H, m); 2.37 (2H, t, J = 5.0Hz); 3.50–4.20 3H, m); 6.59 (1H, t, J = 73Hz); 7.61 (4H, s); 7.10–7.85 (4H, m); 8.17 (1H, bs) |
| XII | 1.40–1.90 (4H, m); 3.22 (3H, s); 3.20–4.00 (5H, m); 6.51 (1H, t, J = 73Hz); 6.90–7.80 (8H, m); 8.00 (1H, bs) |

Certain examples of the compositions of the compounds of the present invention as insecticides are provided for purposes of illustration only and are not intended to be limiting the present invention. In the compositions, all parts are indicated by weight.

Composition 1 Emulsifiable concentrate

Compound No. 1: 10 wt. parts
Xylene: 80 wt. parts
Sorpol 2680 (Toho Chem.): 10 wt. parts The components were uniformly mixed to prepare an emulsifiable concentrate. The emulsifiable concentrate was diluted with water to 50–100,000 times and it was sprayed in amounts of 10–500 liter/10 ares.

As the active ingredient, Compound No. 2, 5, 6, 11, 14, 26, 28, 31, 32, 34, 37, 38, 41, 45, 47 and 48 were used.

Composition 2 Oil solution

Compound No. 2: 50 wt. parts
Methyl cellosolve: 50 wt. parts

The components were uniformly mixed to obtain an oily solution.

The oil solution was applied in amounts of 0.1 to 50 ml./m$^2$ to a drain or puddle or in amounts of 10–100 ml./10 acres by airplane spray.

Composition 3 Wettable powder

Compound No. 5: 25 wt. parts
Zeeklite PFP: 65 wt. parts
Carplex #80 : 2 wt. parts
Sorpol 5050: 2 wt. parts
Sodium ligninesulfonate: 6 wt. parts The components were uniformly ground and mixed to obtain a wettable powder. The wettable powder was diluted with 100 to 250,000 times of water and it was sprayed in amounts of 20 to 500 liter/10 ares.

Composition 4 Dust

Compound No. 11: 3.0 wt. parts
Carplex #80: 0.5 wt. parts
Clay: 95 wt. parts
Diisopropyl phosphate: 1.5 wt. parts The components were uniformly mixed to obtain a dust. The dust was applied in amounts of 0.03 to 15 kg/10 ares.

Composition 5 Bait Poison

Wheat bran: 52 wt. parts
Rice bran: 15 wt. parts
Wheat powder: 30 wt. parts
Raw sugar (muscovado): 3 wt. parts The components were uniformly mixed and Compound No. 31 was added at a ratio of 0.2% based on the total components. Water was added at a ratio of 50% based on the total components and the mixture was granulated by a pelleter and dried at 50° to 60° C. by hot air. The resulting bait poison was placed in amounts of 0.1–5 g./m² around a root of a plant.

As the active ingredient, Compound No. 1, 2, 3, 4, 5, 6, 8, 9, 11, 12, 14, 18, 24, 26, 28, 30, 32, 36, 39, 40, 43, 46, 47 and 58 were used.

The insecticidal activities of the compounds of the present invention will be illustrated by tests.

Experiment 1

Contact test for killing adult houseflies

A 1 ml. of 100 ppm solution of each active ingredient of the present invention in acetone was dropped onto the bottom of a Petri dish (9 cm) and was spread uniformly over the surface of the dish. Acetone was completely evaporated at room temperature. Ten adult houseflies were placed in the dish, which was covered with a plastic cover having many holes. The Petri dish was maintained in a constant temperature room at 25° C. for 48 hours and each percent mortality of the houseflies were determined. The test was repeated twice and the results are shown in Table 2.

TABLE 2:

| Active ingredient | Percent mortality (%) |
|---|---|
| Compound No. 3 | 100 |
| No. 11 | 100 |
| No. 26 | 100 |

Experiment 2

Contact test for killing green rice leafhopper

Stems and leaves of a rice seedling were dipped in each emulsion of each composition of the active ingredient of the present invention or Reference Compound (100 ppm) for 10 seconds and were dried in air. The stems and leaves were covered with a glass cylinder and adult green rice leafhoppers which are resistant to the conventional organic phosphorus type insecticides were released into the glass clinder which was covered with a cover having holes and was maintained in a constant temperature room at 25° C. for 48 hours and each percent mortality was determined.

The results are shown in Table 3.

TABLE 3:

| Active ingredient | Percent mortality (%) |
|---|---|
| Compound No. 11 | 100 |
| No. 14 | 100 |
| Reference Comp. A | 20 |

Note:
Reference Compound A:

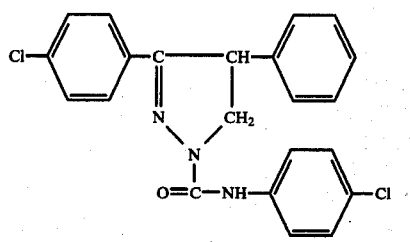

(Japanese Unexamined Patent Publication No. 41358/1976)

Experiment 3

Contact test for killing Common cutworm

Leaves of cabbage were dipped in each aqueous emulsion of each active ingredient of the compounds of the invention or the reference for 10 seconds. The leaves were taken up and dried in air and put in a Petri dish. Common cutworms (second instar) were put in the Petri dish which was covered with a cover having many holes. The Petri dish was maintained in a constant temperature room at 25° C. for 48 hours and each percent mortality was determined. The results are shown in Table 4.

TABLE 4

| Active ingredient | Concentration (ppm) | Percent morality (%) |
|---|---|---|
| Compound No. 1 | 1.25 | 100 |
| No. 2 | 1.25 | 100 |
| No. 3 | 1.25 | 100 |
| No. 8 | 1.25 | 100 |
| No. 9 | 1.25 | 100 |
| No. 10 | 1.25 | 100 |
| No. 11 | 1.25 | 100 |
| No. 12 | 1.25 | 100 |
| No. 14 | 1.25 | 100 |
| No. 18 | 1.25 | 100 |
| No. 24 | 1.25 | 100 |
| No. 26 | 1.25 | 100 |
| No. 28 | 1.25 | 100 |
| No. 30 | 1.25 | 100 |
| No. 31 | 1.25 | 100 |
| No. 32 | 1.25 | 100 |
| Reference Comp. A | 1.25 | 70 |
| Compound No. 37 | 10 | 100 |
| No. 39 | 10 | 100 |
| No. 40 | 10 | 100 |
| No. 43 | 10 | 100 |
| No. 47 | 10 | 100 |
| No. 48 | 10 | 100 |
| No. 51 | 10 | 100 |
| Reference Comp. B | 10 | 40 |
| C | 10 | 70 |
| D | 10 | 60 |

Note:
Reference Compound A:

TABLE 4-continued

| Active ingredient | Concentration (ppm) | Percent morality (%) |
|---|---|---|

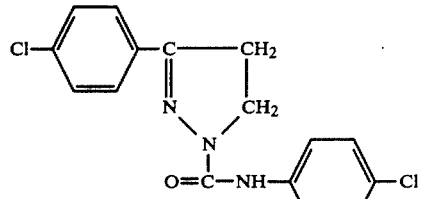

(Japanese Unexamined Patent Publication No. 41358/1976)

Reference Compound B:

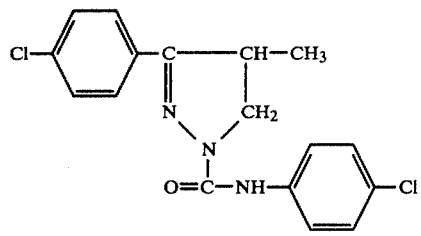

(Japanese Unexamined Patent Publication No. 87028/1973)

Reference Compound C:

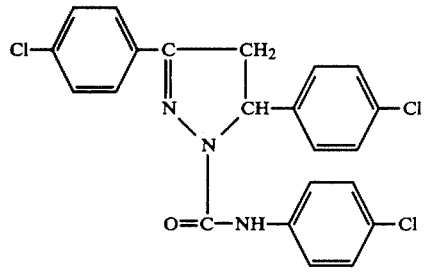

(Japanese Unexamined Patent Publication No. 41358/1976)

Reference Compound D:

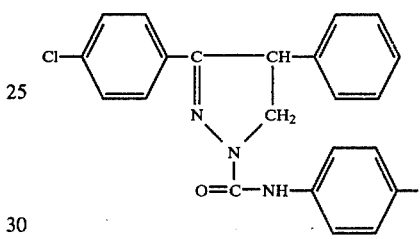

(Japanese Unexamined Patent Publication No. 87028/1973)

Experiment 4

Contact test for killing Twenty-eight-spotted Ladybeetle

Leaves of tomato were dipped in 10 ppm aqueous emulsion of each active ingredient of the compounds of the present invention and the reference for 10 seconds. The leaves were taken up and dried in air and put in a Petri dish. Ten of Twenty-eight-spotted Ladybeetles (second instar) were put in the Petri dish which was covered with a cover. The Petri dish was maintained in a constant temperature room at 25° C. for 48 hours and percent mortality was determined. The tests were carried out in two groups. The results are shown in Table 5.

TABLE 5:

| Active ingredient | Percent mortality (%) |
|---|---|
| Compound No. 2 | 100 |
| No. 5 | 100 |
| No. 11 | 100 |
| No. 12 | 100 |
| No. 14 | 100 |
| No. 15 | 100 |
| No. 18 | 100 |
| No. 26 | 100 |
| No. 28 | 100 |
| No. 29 | 100 |
| No. 31 | 100 |
| No. 32 | 100 |
| No. 40 | 100 |
| Reference Comp. A | 70 |

Note:
Reference Compound A:

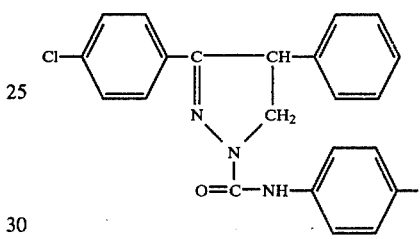

(Japanese Unexamined Patent Publication No. 41358/1976)

Experiment 5

Test for killing diamond back moth

Leaves of cabbage were dipped in each aqueous emulsion of each active ingredient of the compounds of the invention or the reference (1 ppm) for 10 seconds. The leaves were taken up and dried in air and put in a Petri dish. Lavae of Diamond back moth were put in the Petri dish which was covered with a cover having many holes. The Petri dish was maintained in a constant temperature room at 25° C. for 48 hours and each percent mortality was determined. The results are shown in Table 6.

TABLE 6:

| Active ingredient | Percent mortality (%) |
|---|---|
| Compound No. 5 | 100 |
| No. 6 | 100 |
| No. 8 | 100 |
| No. 9 | 100 |
| No. 11 | 100 |
| No. 12 | 100 |
| No. 14 | 100 |
| No. 18 | 100 |
| No. 23 | 100 |
| No. 26 | 100 |
| No. 28 | 100 |
| No. 29 | 100 |
| No. 30 | 100 |
| No. 31 | 100 |
| No. 32 | 100 |

TABLE 6:-continued

| Active ingredient | Percent mortality (%) |
|---|---|
| Reference Comp. A | 30 |

Note:

Reference Compound A:

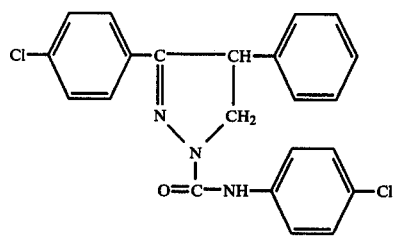

(Japanese Unexamined Patent Publication No. 41358/1976)

Experiment 6

Fish-toxicity to kill fish

In a glass vessel having a diameter of 20 cm and a height of 10 cm, 2 liter of water was charged. A solution of each compound of the invention or the reference in methanol was added to give a concentration of 0.5 ppm. The vessel was maintained in a constant temperature tank at 25° C. and ten of kill fish were put in the vessel and timely observed. Table 7 shows survival percents after 72 hours.

TABLE 7:

| Active ingredient | Survival percent (%) |
|---|---|
| Compound No. 1 | 100 |
| No. 5 | 100 |
| No. 12 | 100 |
| No. 19 | 100 |
| No. 23 | 100 |
| No. 24 | 100 |
| Reference Comp. A | 0 |

Note:

Reference Compound A:

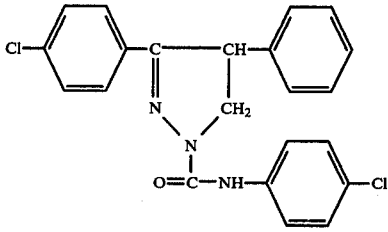

(Japanese Unexamined Patent Publication No. 41358/1976)

We claim:

1. A pyrazoline derivative having the formula

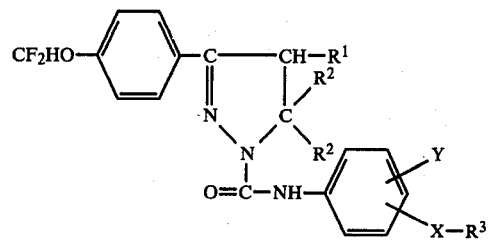

wherein $R^1$ represents hydrogen atom, a lower alkyl group, $(CH_2)_nCN$ group, $(CH_2)_nOR$ group, phenyl group or a halogen-substituted phenyl group; $R^2$ represents hydrogen atom or methyl group; Y represents hydrogen atom or chlorine atom; X represents oxygen atom, sulfur atom, sulfinyl or sulfonyl group; $R^3$ represents a halogen-substituted lower alkyl group; and n is integer 1 to 3 and R represents a lower alkyl group.

2. The pyrazoline derivative according to claim 1 having the formula [II]

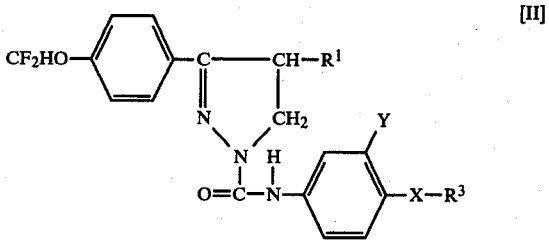

3. The pyrazoline derivative according to claim 2 having the formula [II] wherein Y represents hydrogen atom.

4. The pyrazoline derivative according to claim 3 having the formula [II] wherein $R^1$ represents phenyl group or a halogen-substituted phenyl group.

5. 1-(4-Trifluoromethylthiophenylcarbamoyl)-3-(4-difluoromethoxyphenyl)-4-phenyl-2-pyrazoline.

6. 1-(4-Trifluoromethylsulfinylphenylcarbamoyl)-3-(4-difluoromethoxyphenyl)-4-phenyl-2-pyrazoline.

7. 1-(4-Trifluoromethylsulfonylphenylcarbamoyl)-3-(4-difluoromethoxyphenyl)-4-phenyl-2-pyrazoline.

8. 1-(4-Difluoromethoxyphenylcarbamoyl)-3-(4-difluoromethoxyphenyl)-4-phenyl-2-pyrazoline.

9. 1-[4-(1',1',2',2'-Tetrafluoroethoxy)phenylcarbamoyl]-3-(4-(4-difluoromethoxyphenyl)-4-phenyl-2-pyrazoline.

10. 1-(4-Trifluoromethoxyphenylcarbamoyl)-3-(4-difluoromethoxyphenyl)-4-phenyl-2-pyrazoline.

11. 1-(4-Trifluoromethoxyphenylcarbamoyl)-3-(4-difluoromethoxyphenyl)-4-(4-chlorophenyl)-2-pyrazoline.

12. 1-(4-Trifluoromethylthiophenylcarbamoyl)-3-(4-difluoromethoxyphenyl)-4-(4-fluorophenyl)-2-pyrazoline.

13. 1-(4-Trifluoromethoxyphenylcarbamoyl)-3-(4-difluoromethoxyphenyl)-4-(4-fluorophenyl)-2-pyrazoline.

14. An insecticide which comprises a carrier and an insecticidally effective amount of a pyrazoline derivative defined in claim 1, 2, 3, 4, 5, 6, 7, 8, 9, 10, 11, 12 or 13 as an active ingredient.

* * * * *

UNITED STATES PATENT AND TRADEMARK OFFICE
CERTIFICATE OF CORRECTION

PATENT NO. : 4,464,386

DATED : August 7, 1984

INVENTOR(S) : Kiyomi Ozawa et al

It is certified that error appears in the above-identified patent and that said Letters Patent is hereby corrected as shown below:

On the title page

Please list the following two inventors in addition to Letters Patent:

-- [75] Inventors
   Masayoshi Hirose   Saitama, Japan
   Masaki Kudo   Saitama, Japan --

Please list the Foreign Application Priority Data

-- [30] Japanese Patent Application No. 4326/1982, filed on January 14, 1982 --

Signed and Sealed this

Eighteenth Day of December 1984

[SEAL]

Attest:

Attesting Officer

GERALD J. MOSSINGHOFF

Commissioner of Patents and Trademarks